Oct. 23, 1956 M. MALANDRONE Plant Pat. 1,524
ROSE PLANT
Filed Nov. 29, 1955
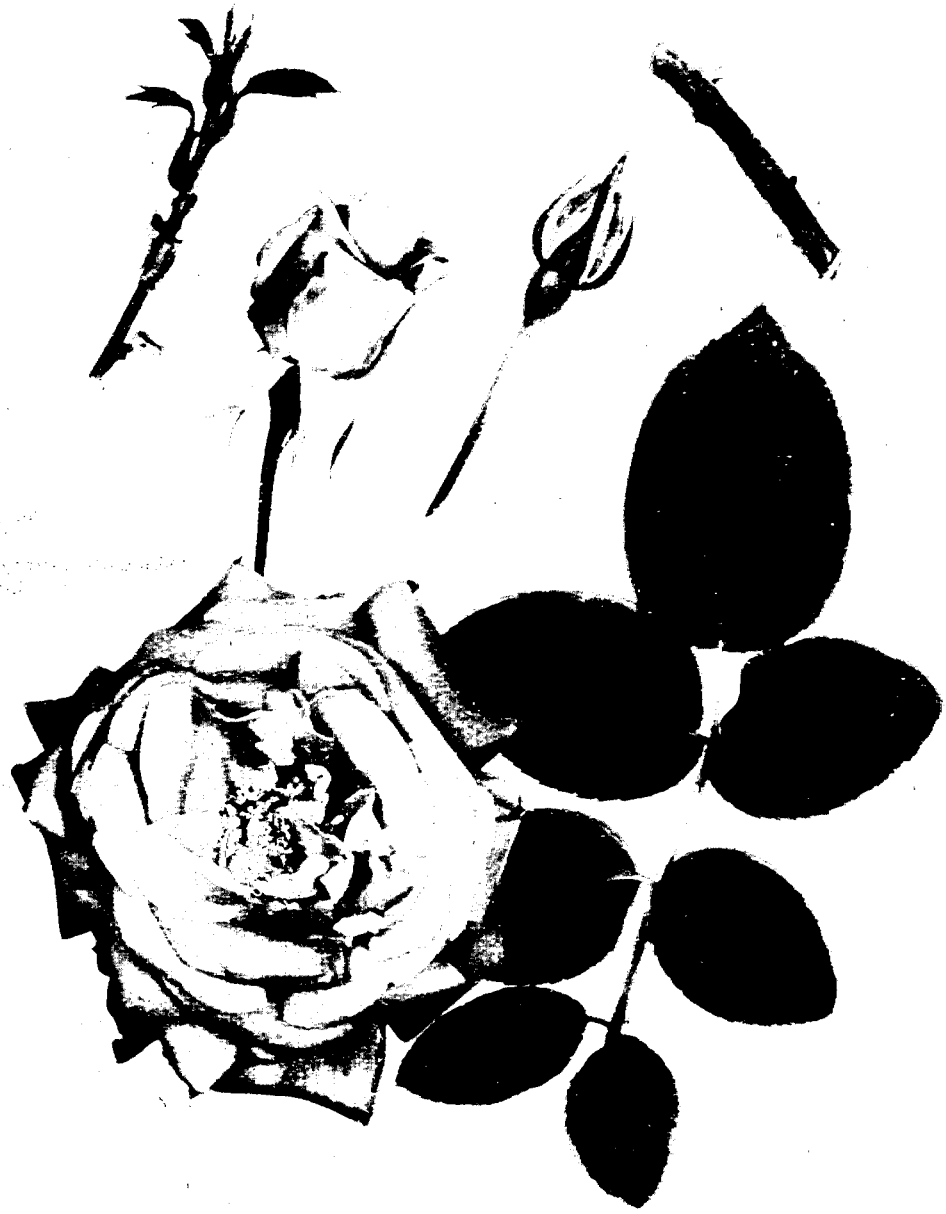
Inventor
M. Malandrone
By Robb & Robb
Attorneys United States Patent Office Plant Pat. 1,524
Patented Oct. 23, 1956

1,524

ROSE PLANT

Michele Malandrone, Oakland, Calif., assignor to Jackson & Perkins Company, Newark, N. Y., a corporation of New York Application November 29, 1955, Serial No. 549,903

1 Claim. (Cl. 47—61)

The present invention relates to a new and distinct variety of rose plant of the climber class, which was originated by me by crossing the variety "Charlotte Armstrong" (Plant Patent No. 455) with an unnamed and unpatented seedling derived from a cross of the hybrid tea variety "Pink Delight" (unpatented) and unnamed and unpatented seedling of "New Dawn" (Plant Patent No. 1).

The primary objective of this breeding was to produce a large-flowered everblooming climber. This objective was fully achieved by repeated crossings on seedlings of the variety "New Dawn," which is an everblooming climber, but the flowers of which are relatively small in size. In addition to the increased size of the flowers of my new variety, other improvements therein have been attained, as evidenced by the following features which particularly differentiate the new variety from its parents, as well as from all other varieties of its class of which I am aware:

(1) An improved hardiness which differentiates the new variety from the more tender climbing sports of hybrid tea varieties;

(2) The dark green foliage which is especially desirable and attractive in a climber;

(3) The large size of the blooms and frequent rebloming habit which is unusual in a climbing rose of such size; and (4) The distinctive Tyrian Rose, lightly overcast with Rose Red, general color tonality of the flowers.

Asexual reproduction of my new variety by budding, as performed at Newark, New York and also at Pleasanton, California, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.

*Seed parent.*—"Charlotte Armstrong."

*Pollen parent.*—An unnamed and undisseminated seedling derived from a cross of the hybrid tea variety "Pink Delight" and an unnamed seedling of the variety "New Dawn."

Classification:

*Botanic.*—Climber.

*Commercial.*—Climber.

FLOWER (Observations made from specimens grown outdoors at Newark, New York, in the latter part of the month of August and in the early morning.)

Blooming habit: Recurrent—intermittent all summer.

Bud:

*Size.*—Medium.

*Form.*—Ovoid; is not affected by wet or hot weather.

*Color.*—When sepals first divide—Oxblood Red, Plate 1. When petals begin to unfurl—Bordeaux, Plate 12, lightly overcast with Indian Lake, Plate 26. When half-blown; inside of petals—Tyrian Rose, Plate 12, overcast with Rose Red, Plate 12; reverse of petals—Rose Red, Plate 12, lightly overcast with Spectrum Red, Plate 1.

*Sepals.*—Slightly branched; curl back when petals begin to unfurl. Color: inside—Corydalis Green, Plate 41; outside—Jade Green, Plate 31.

*Calyx.*—Color—Jade Green, Plate 31. Shape—funnel. Size—small. Aspect—smooth. Odor when rubbed—none.

*Peduncle.*—Length — medium. Aspect — smooth. Strength—erect; slender. Color—Light Hellebore Green, Plate 17.

*Opening.*—Opens up well; is not affected by adverse weather conditions.

Bloom:

*Size.*—Large. Average size when fully expanded—from 4½ inches to 5 inches.

*Borne.*—Sometimes singly and sometimes several together.

*Stems.*—Medium length; normal strength.

*Form (when first open).*—From high-centered to cupped. Permanence—retains its form to the end.

*Petalage.*—Double (full but open center). Number of petals under normal conditions—35.

*Color.*—Center of flower—Rose Red, Plate 12, lightly overcast with Tyrian Rose, Plate 12. Outer petals—Tyrian Rose, Plate 12. Base of petals (aiglet)—Light Greenish Yellow, Plate 5. Inside of petals—Tyrian Rose, Plate 12, lightly overcast with Rose Red, Plate 12. Reverse of petals—Spinel Red, Plate 26, lightly overcast with Rose Color, Plate 12. General tonality from a distance—Tyrian Rose, Plate 12, lightly overcast with Rose Red, Plate 12.

*Discoloration.*—General tonality at end of first day—Rose Red, Plate 12. Second day—Rose Red, Plate 12, lightly overcast with Tyrian Rose, Plate 12. Third day—Tyrian Rose, Plate 12, lightly overcast with Rose Red, Plate 12.

Petals:

*Texture.*—Leathery; is not affected by wet or hot weather.

*Appearance.*—Inside—satiny; outside—shiny.

*Form.*—Oval.

*Arrangement.*—Informal (with "rags" in center).

*Petaloids in center.*—Few; large.

*Persistence.*—Drop off cleanly.

*Fragrance.*—Moderate. Nature—tea (average hybrid tea scent).

*Lasting quality.*—On the plant—long; as cut flower—long.

GENITAL ORGANS

Stamens, anthers: Small; many; arranged regularly around styles. Color—Light Orange Yellow, Plate 3.

Stamens, filaments (threads): Medium length. Color—Eugenia Red, Plate 13.

Pollen: Color—Salmon Buff, Plate 14.

Styles: Loosely separated; uneven length; short; thin.

Stigmas: Color—Sulphur Yellow, Plate 5.

Ovaries: All enclosed in calyx.

Hips: None.

Seeds: None.

PLANT

Form: Climber.

Growth: Vigorous; upright; from 10 to 12 feet tall.

Foliage: 5 to 7 leaflets.

*Size.*—Medium.

*Quantity.*—Normal.

*Color.*—New foliage: upper side—Yellowish Oil Green, Plate 5, lightly overcast with Oxblood Red, Plate 1; under side—Absinthe Green, Plate 31, lightly overcast with Oxblood Red, Plate 1. Old foliage: Upper side—Dark Cress Green, Plate 31; under side—Light Elm Green, Plate 17.

*Shape.*—Oval pointed.

*Texture.*—Upper side—leathery; under side—smooth.

*Ribs and veins.*—Ordinary.

*Edge.*—Serrated (saw-toothed).

*Serration.*—Both double and single; small.

*Leaf stem.*—Color—Absinthe Green, Plate 31. under side—prickles.

*Stipules.*—Medium length; slightly bearded.

Wood:

*New wood.*—Color—Kronberg's Green, Plate 31. Bark—smooth.

*Old wood.*—Color—Cress green, Plate 31. Bark—smooth.

Thorns:

*Thorns.*—Quantity: On main stalks from base—few; on laterals from stalk—few. Form—medium length; some hooked downward and some hooked upward; with narrow base. Color (when young)—Carmine, Plate 1. Position—irregular.

*Prickles.*—Quantity: On main stalks—none; on laterals—none.

*Short needles.*—Quantity: On main stalks—none; on laterals—none.

I claim:

A new and distinct variety of rose plant of the climber class, substantially as herein shown and described, characterized particularly as to novelty by its improved hardiness, its dark green foliage, its large flowers and unusual frequent re-blooming habit thereof, and the distinctive Tyrian Rose, lightly overcast with Rose Red, general color tonality of its flowers.

No references cited.